United States Patent
Setchell et al.

(10) Patent No.: US 10,499,785 B2
(45) Date of Patent: Dec. 10, 2019

(54) CLEANLINESS MONITORING

(71) Applicant: Spot You More, Inc., Raleigh, NC (US)

(72) Inventors: Joel R. Setchell, Advance, NC (US); James D. Haley, Winston-Salem, NC (US)

(73) Assignee: Spot You More, Inc., Raleigh, NC (US)

( * ) Notice: Subject to any disclaimer, the term of this patent is extended or adjusted under 35 U.S.C. 154(b) by 185 days.

(21) Appl. No.: 15/660,202

(22) Filed: Jul. 26, 2017

(65) Prior Publication Data

US 2018/0028038 A1 Feb. 1, 2018

Related U.S. Application Data

(60) Provisional application No. 62/367,625, filed on Jul. 27, 2016.

(51) Int. Cl.
*A47L 13/20* (2006.01)
*A61B 5/103* (2006.01)
(Continued)

(52) U.S. Cl.
CPC .......... *A47L 13/20* (2013.01); *A47L 11/4008* (2013.01); *A47L 13/10* (2013.01); *A47L 13/42* (2013.01); *A61B 5/103* (2013.01); *G01C 19/02* (2013.01); *G01F 23/0007* (2013.01); *G01L 19/0092* (2013.01); *G01N 27/048* (2013.01); *G06Q 10/00* (2013.01); *A47K 10/18* (2013.01); *F21V 31/04* (2013.01); *F25D 23/028* (2013.01);
(Continued)

(58) Field of Classification Search
CPC .......... A47L 13/00; A47L 13/10; A47L 13/12; A47L 13/20; A47L 13/42; A47L 11/4008; B08B 1/00; B08B 1/001; B08B 1/002; B08B 1/003; B08B 1/005; B08B 1/006; B08B 1/007; B08B 1/008; B08B 13/00
USPC .............. 15/105, 228, 4, 319; 340/500, 540, 340/568.1, 665, 603, 605, 545.1, 573.1
See application file for complete search history.

(56) References Cited

U.S. PATENT DOCUMENTS 6,972,677 B2 * 12/2005 Coulthard .............. G06Q 10/10
340/531
8,344,893 B1 * 1/2013 Drammeh ............ G08B 21/245
340/540
(Continued)

FOREIGN PATENT DOCUMENTS

CN          203366133 U    * 12/2013

OTHER PUBLICATIONS

CN-203366133-U translation from Espacenet (Year: 2019).*
International Search Report, International Application No. PCT/US2017/043920, dated Oct. 9, 2017, 4 pgs.

*Primary Examiner* — Joseph J Hail
*Assistant Examiner* — Timothy Brian Brady
(74) *Attorney, Agent, or Firm* — Brinks Gilson & Lione

(57) ABSTRACT

A system for monitoring cleanliness in a store. The system may include a server, a database and at least one sensor. The database may be in communication with the server and may store cleanliness parameters. The system includes at least one sensor configured to transmit measured cleanliness characteristics to the server and the server is configured to transmit a message based on a comparison of the measured cleanliness characteristics and the cleanliness parameters stored in the database.

14 Claims, 2 Drawing Sheets

(51) Int. Cl.
*G01C 19/02* (2006.01)
*G01F 23/00* (2006.01)
*G01L 19/00* (2006.01)
*G01N 27/04* (2006.01)
*A47L 11/40* (2006.01)
*A47L 13/10* (2006.01)
*A47L 13/42* (2006.01)
*G06Q 10/00* (2012.01)
*A47K 10/18* (2006.01)
*F21V 31/04* (2006.01)
*F25D 23/02* (2006.01)
*G01B 11/00* (2006.01)
*H04L 29/08* (2006.01)

(52) U.S. Cl.
CPC .... *G01B 11/005* (2013.01); *G01L 2019/0053* (2013.01); *H04L 67/06* (2013.01)

(56) References Cited

U.S. PATENT DOCUMENTS

| | | | | |
|---|---|---|---|---|
| 2005/0186015 | A1* | 8/2005 | Sacks | A47L 13/22 |
| | | | | 401/139 |
| 2011/0132413 | A1* | 6/2011 | Gans | B08B 1/00 |
| | | | | 134/117 |
| 2014/0022917 | A1* | 1/2014 | Apte | G01S 1/68 |
| | | | | 370/252 |
| 2014/0047930 | A1 | 2/2014 | Schädel et al. | |
| 2014/0259510 | A1* | 9/2014 | Conrad | A47L 13/225 |
| | | | | 15/319 |
| 2014/0259516 | A1* | 9/2014 | Scolari | A47L 13/225 |
| | | | | 15/322 |
| 2015/0327668 | A1* | 11/2015 | Bloch | A46B 15/0012 |
| | | | | 15/22.1 |
| 2016/0179065 | A1* | 6/2016 | Shahabdeen | G05B 15/02 |
| | | | | 700/275 |

\* cited by examiner

CLEANLINESS MONITORING

CROSS-REFERENCE TO RELATED APPLICATIONS

This application claims the benefit of U.S. Provisional Application No. 62/367,625, filed on Jul. 27, 2016, entitled "CLEANLINESS MONITORING," the entire contents of which are incorporated herein by reference.

BACKGROUND

1. Field of the Invention

The present invention generally relates to cleanliness monitoring.

2. Description of Related Art

Convenience stores, especially stores attached to gas stations, are trying to increase revenue and store traffic. Often convenience stores, especially those attached to a gas station, are often used for eating and restroom breaks by travelers. Cleanliness is not always a priority of retail clerks and, therefore, may degrade over time.

SUMMARY

The present disclosure describes a system for cleanliness monitoring, for example at a convenience store.

The system may include a server, a database, and a sensor. The database in communication with the server and storing cleanliness parameters. The sensor may transmit measured cleanliness characteristics to the server. The server may generate and transmit a message based on a comparison of the measured cleanliness characteristics and the cleanliness parameters stored in the database.

The message may be transmitted to a consumer in response to a profile associated with the consumer including a cleanliness importance setting and/or a location of the consumer. The message may be transmitted by the server to a store clerk, a store manager, or an equipment service company.

The sensor may measure a location of a mop, a pressure applied to the mop, a water overflow, a door usage, a sink usage, a toilet usage, an amount of paper towels or toilet paper remaining in a dispenser. In some implementations, the location of the mop may be measured based on triangulation of three sensors.

In some aspects of this disclosure the system may include a mop. The mop may include a handle, a mop head assembly, a sensor, a processor, and a transmitter. The mop head assembly may be attached to the handle. The sensor may measure a usage characteristic of the mop and generate a usage measurement signal. The processor may receive the usage measurement signal. The transmitter may receive usage information from the processor and transmit a message based on the usage information.

The sensor may measure a motion of the mop, pressure applied to the mop and/or moisture of a mop head material. As such, the sensor may be an accelerometer, a gyroscope, a pressure sensor, or a moisture sensor.

Further objects, features and advantages of this invention will become readily apparent to persons skilled in the art after a review of the following description, with reference to the drawings and claims that are appended to and form a part of this specification.

DETAILED DESCRIPTION

Sensors may be used in conjunction with retail locations such as convenience stores and gas stations. The sensors may be at fixed locations within the stores or may be attached to or integrated within certain devices movable within the store. The sensors fixed within the stores may also interact with the devices to provide location of the devices within the store. Sensors attached to or integrated within the devices may provide information regarding the use of the device and/or location of the device. Further, information may be provided that relate the usage characteristics to one another or time intervals to interpret how the device is being used. The analysis may compare usage of the device to proper usage characteristics. Analysis of the usage may be based on defined logic and thresholds defined within the device, a local server, or a cloud based analytics platform. The local server or analytics platform may house the data pushed up from the sensor devices, notification alerts may be triggered based on certain events. Certain data may be distributed by the server to relevant stakeholders based on a defined frequency or immediately based on certain conditions being met.

Data that is to be collected by the smart sensors and pushed to the cloud to be analyzed includes, but may not be limited to: Bathroom throughput (# of people entering, and exiting), Time between entry, Length of visit (dwell time), Mop location, Mop movement including duration and form, Mop physical characteristics including Saturation (did mop get wet?) and Head quality (does mop head need to be changed). Further, other smart sensors may also monitor Soap level, Water level in toilet, Water level on floor, Paper towel supply, and Toilet paper supply.

The relevant stakeholder groups that will receive notification alerts and/or data include, but may not be limited to store clerks, store managers, CPGs, consumers, and equipment OEMs. As a general rule, each notification trigger and data distribution set discussed in this disclosure can be mapped (one to one [1-1] and/or one to many [1-n]) to each of the delivery channels/mechanisms discussed.

Figure 1:
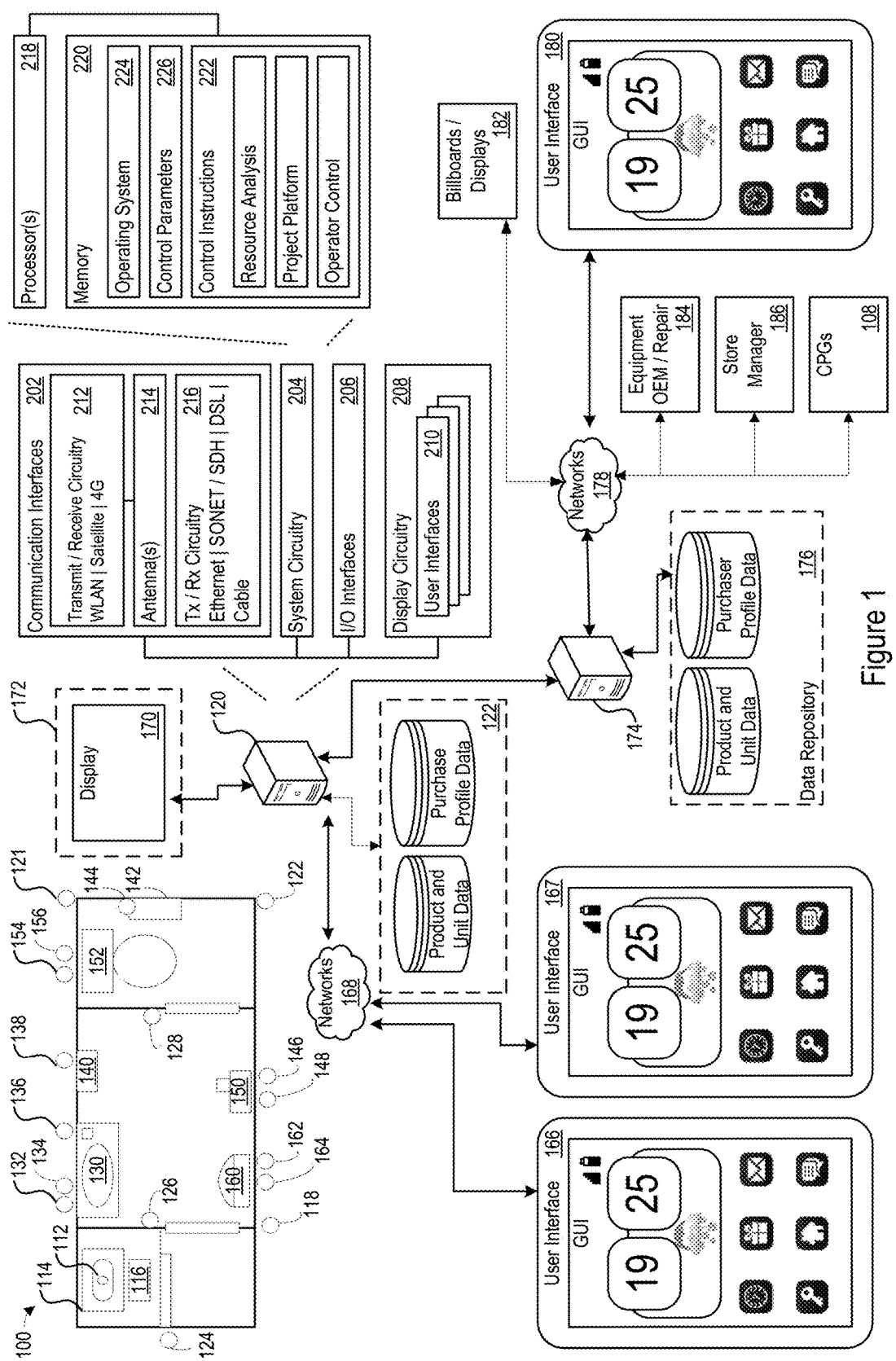
FIG. 1 is a block diagram of a system for cleanliness monitoring.

FIG. 1 is a block diagram of a cleanliness monitoring system 100. The system 100 may include a mop 112, a charging station 113, a bucket 116, and a number of other sensors in communication with a server 120. The system may include a number of sensors monitoring different cleanliness characteristics at a retail location such as a convenience store. In one example, a restroom of a convenience store is monitored by the system 100. Although, the system may interact with multiple sensors at multiple convenience store locations simultaneously. The sensors may be smart sensors and therefore may receive and/or send data to a monitoring production server either directly or through a hub. A smart sensor may include a processor. The processor may allow the sensor to sample and transmit data upon receipt of a command to do so and/or continuously sample data to provide a continuous stream of data with regard to the characteristic being monitored, and/or monitor the data and evaluate if the data exceeds certain defined thresholds and send an alert in response to the monitored characteristic exceeding one or more thresholds. The alert may include and alert classification as well as the monitored data. The processor may also provide for the measurement unit to be calibrated and/or reset at the location of the sensor or remotely from a server. The sensor may include a display and/or end-user interface (e.g. buttons or switches, etc.) for setting and reviewing real time data as well as setting and monitoring alert information or threshold information. The sensors monitor characteristics related to cleanliness, such as usage, frequency of usage, water levels, availability of cleanliness related products, etc. Alerts may be generated in response to any of cleanliness related characteristics noted herein, either based on a threshold or a comparison with other product or unit characteristics.

Smart sensors, for example infrared proximity sensors, may be placed on the wall of the bathroom. Sensors may connect to a smart mop and embedded accelerometer via Bluetooth Low Energy (BLE) signal. Sensors may collect data on the number of patrons entering and exiting the bathroom, and may also monitor when, how frequently, and for how long the bathroom has been mopped. Other use cases beyond this baseline are explored in the below document (e.g. Soap levels, Water level in toilet, Water level on floor, Paper towel supply, Toilet paper supply).

Figure 2:
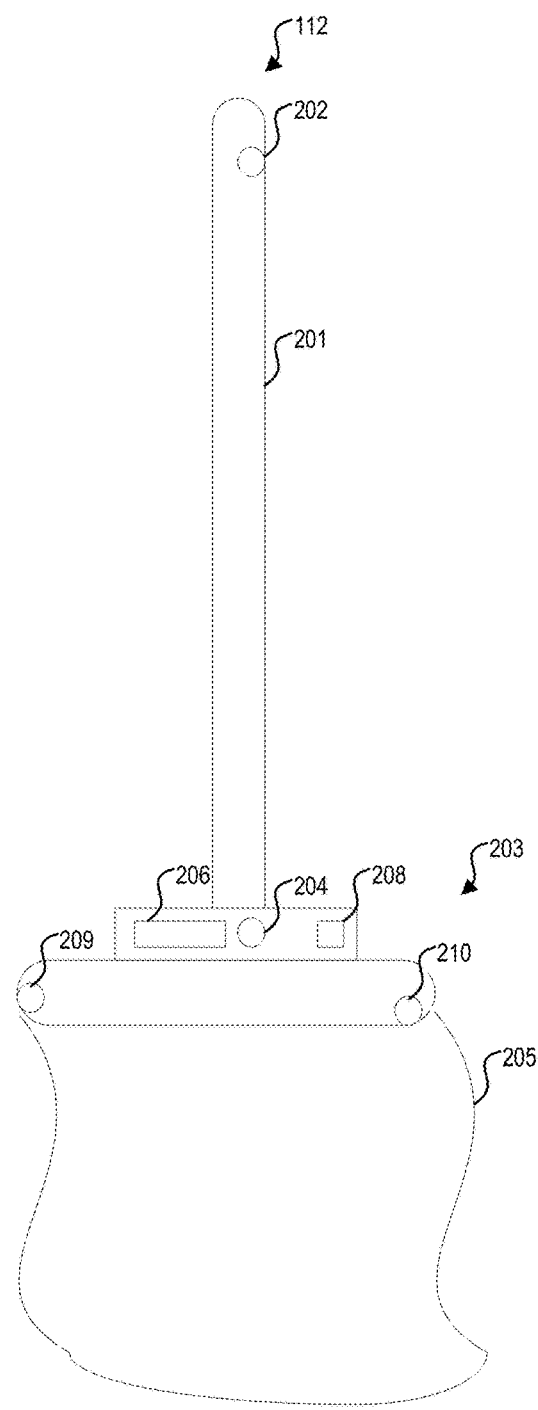
FIG. 2 is an illustration of a mop assembly for cleanliness monitoring.

FIG. 2 illustrates additional detail of the mop 112. The mop 112 includes a handle 201 extending from a mop head assembly 203. The mop head assembly 203 may include a replaceable mop head material 205 that may be changed due to wear and damage over the life of the mop 112. Mop head assembly 203 may also include a processor 206 and multiple sensors. The mop head assembly may include a motion sensor 204 to detect and/or characterize the movement of the mop 112 during usage. The motion sensor 204 may include one or more accelerometers to identify the motion of the mop 112 along multiple axes, for example one axis along the handle and two axis perpendicular to the handle. Further, the motion sensor 204 may include a gyroscope or other angular sensors to determine the orientation of the mop 112 during its use. As such, the processor 206 may analyze the motion characteristics of the mop including for example, acceleration, velocity, tilt, pressure, or other characteristics to determine whether the mop is being used properly. Such determination may be based on various thresholds with regard to one or more of the motion characteristics and/or comparison with a template motion profile over time to determine if the actual motion of the mop matches or is similar to a predetermined motion profile. In some examples, similarity may be determined by a threshold of the correlation between the actual motion and the predetermined motion profile.

Further, the processor 206 may be in communication with pressure sensor 209 and moisture sensor 210. Pressure sensor 209 may provide a signal indicating the amount of pressure being put on the mop head material 205 through the handle 201. Moisture sensor 210 may determine whether the mop head material 205 has been saturated for example, placed in a bucket full of water and/or soap to conduct the mopping. As such, the motion of the mop from sensor 204, the pressure applied to the mop 209 and the moisture of the mop head material from sensor 210 may be used in conjunction to determine proper usage of the mop due to thresholds on each of those characteristics and/or in comparison to various stored usage profiles.

The mop 112 may include a power interface 208. The power interface 208 may include a connector that may provide power to the processor and sensors within the mop 112. Further, the power interface 208 may include a battery to store power for the processor and sensors during use. The power interface 208 may allow for direct contact to convey the power or may use a wireless charging technology for example inductive charging such that direct contact with the mop is not required to perform charging activity. In some implementations, the charging interface 208 may include a photocell allowing the battery to be charged using light energy that is projected onto a photo panel and stored in a battery for later use by the processor and sensors.

The processor 206 may also control a transmitter 202. The transmitter 202 may communicate information about the motion of the mop, pressure applied to the mop, and/or moisture of the mop head to a server remote from the mop 112. The processor 206 may transmit raw data from the sensors and/or may reduce the data transmitted by applying thresholds and/or profile comparisons prior to them transmitting the results of the thresholds and/or comparisons or alerts if the thresholds or comparisons are exceeded or beyond a predetermined value or frequency. In addition, the transmitter 202 may be used in conjunction with sensors within the retail location to determine a position of the mop 112 within the retail location.

Referring again to FIG. 1, the charging station 114 may be provided to interface with the mop 112. The charging station 114 may include a power interface such as a connector or inductive wireless charging panel to inner provide power to the power interface of the mop 112. The mop 112 may be used with a bucket 116. In some implementations, the bucket 116 may include a processor and transmitter to identify the position of the bucket 116 with regard to sensors placed within the retail location. Further, the bucket 116 may include a moisture sensor and/or a fill level sensor to identify that the bucket 116 is properly filled when used in conjunction with the mop 112. The mop 112, the charging station 114, and the bucket 116 may be stored in a closet which may be near a restroom facility. The closet may include a door and a sensor 124 may be positioned to interface with the door to determine when the door is opened or closed. The opening and closing of the door as determined by sensor 124 may be indicative of the mop and bucket being accessed and may be used by a cleanliness monitoring server to trigger certain monitoring activities and/or satisfy certain action requests. The sensor 124 may be proximity, displacement, motion, or other sensor configured to identify the opening and closing of the door.

Similarly, sensor 126 may monitor the opening and closing of a bathroom door providing access to the bathroom from the retail area of the store. Sensor 126 may be used to determine a mount and/or frequency access to the bathroom. In addition, sensor 128 may be configured to determine whether a door to a stall is opened or closed and as such may be used to determine the number of accesses and/or frequency of access to a particular stall in a particular bathroom. Sensors 126 and 128 may be proximity, displacement, motion, or other sensor configured to identify the opening and closing of the door.

As the mop 112 and/or bucket 116 is moved into the restroom, sensor 118 may communicate with the transmitter for example, transmitter 102 of mop 112, to determine a location of the mop. In one implementation, the strength of the transmitted signal may be used to determine the proximity with regard to sensor 118 and if the proximity is within a certain distance based on signal strength, the mop will be determined to have entered the restroom. In another implementation, multiple sensors may be used to determine the location of the mop and/or bucket within the restroom using the signal strength and/or other signal characteristic to triangulate a position of the mop within the restroom. For example, the sensor 118 may be positioned within a first location, for example, a first corner of the room. A second sensor 121 may be positioned in a second position, for example, a second corner of the room opposite from the first sensor 118. A third sensor 122 may be located in a third position for example, a third corner of the room. Each of the sensors may communicate with the transmitter 102 of the mop 112 to determine a position of the mop and based on the comparison between signal characteristics received by each sensor 118, 121, 122, the position of the mop with regard to each of the sensors may be determined for example, by a triangulation method.

In addition, a sink 130 may be located in the restroom. The sink may include a number of sensors to monitor various characteristics of the sink. For example, sensor 132 may measure use of the sink. For example, sensor 132 may be a proximity sensor to determine when a person has put their hands under the faucet and/or when the person's body has moved close to the sink counter. In some implementations, the sensor 132 may be a water flow sensor to determine that the water is flowing from the faucet. Further, an overflow sensor 134 may be provided to determine if the water level in the sink has exceeded a predetermined threshold. In addition, a fill sensor 136 may monitor the usage and/or amount of soap provided in a soap dispenser located proximate the sink. The fill sensor may be a weight sensor, or a proximity sensor, or displacement sensor configured in a manner to determine an amount of soap used from and/or remaining in the soap dispenser. In addition, a towel dispenser 140 may be provided in the restroom. The sensor 138 may be provided to monitor the amount of towels available in the towel dispenser 140. The sensor 138 again, may be a weight, proximity, displacement, or other sensor configured to measure the amount of towels remaining and/or the amount of towels that have been used from the towel dispenser 140. In addition, a toilet paper dispenser 142 may be provided in a stall of the restroom in a sensor 144 may measure the amount of toilet paper used and/or left available in the toilet paper dispenser 142. Again, the toilet paper dispenser may be a weight sensor, proximity sensor, or displacement sensor configured to measure the amount of toilet paper in the dispenser 142.

The restroom may also include a hand dryer 150. The hand dryer 150 may include a sensor 146 to determine the activation of the hand dryer 150. The sensor 146 may be used to determine the number and/or frequency of activations of the hand dryer 150. Further, a temperature sensor 148 may be used to determine the temperature of the air being blown the hand dryer 150.

The bathroom may include a toilet 152. The toilet 152 may include a sensor 154 which may be used to determine the activation or flush of the toilet as such, the sensor 154 may be used to determine the number of flushes and/or the frequency of the flushing of the toilet. In addition, the sensor 154 may be used to determine if the toilet 152 is continuously flushing due to a stuck handle and/or other defective mechanism. Further, a fill sensor 156 may measure the water level in the toilet bowl and/or tank to determine whether an overflow scenario has occurred.

The bathroom may include a toilet 160. The toilet 160 may include a sensor 162 which may be used to determine the activation or flush of the toilet as such, the sensor 162 may be used to determine the number of flushes and/or the frequency of the flushing of the toilet. In addition, the sensor 162 may be used to determine if the toilet 160 is continuously flushing due to a stuck handle and/or other mechanism. Further, a fill sensor 164 may measure the water level in the toilet bowl and/or tank to determine whether an overflow scenario has occurred.

Alerts may be generated based on measured cleanliness characteristics. The store clerk may be notified to restock or perform maintenance tasks. This information may also be used to generate electronic coupons or in store advertisements in response to the measured characteristics. (e.g. if it is below a threshold offers such as discounts may be given) Data from these sensors may be communicated to a router or server 120 via a network 118. The network may be a wired network and/or a wireless network. As such, the sensors may include a wireless transmitter to connect to the server 120 via a wireless network such as Wi-Fi, BlueTooth, etc.

Upon receiving the data from the sensors the server 120 may store the data locally in a storage device 122. The server may also analyze the data and determine certain thresholds based on the characteristics of the sensor exceeding a certain value, or based on the comparison between various sensors, or based on an alert provided from a particular sensor the server 120 may communicate with a mobile device 166 that may be configured with an application for notifying a store clerk with an action needed to be taken with regard to maintenance or restocking. In addition, the server 120 may communicate with a mobile device 167 from a consumer based on an application loaded on the mobile device 167.

The application may allow the user to receive communication from a local network within the store 110. The application may allow the mobile device 167 to provide a user interface to present offers and/or electronic coupons to the consumer in response to the characteristics monitored by the smart sensors and/or a comparison of the smart sensors and/or a comparison of the monitored data with a threshold. In addition, the server 120 may be in communication with a display device 170 located within the store or on the store grounds as noted by box 172. The display 170 may be a public display, for example, a monitored unit or sign display to provide an offer or message to a consumer in response to cleanliness information. The server 120 may communicate with an external server 174 located in a remote location such as corporate headquarters. The server 174 may receive data from the server 120. The server 120 may push the data to the server 174 and/or, the server 174 may request the data from the server 120. The data may be streamed in real time to the server 174 or accumulated and provided in batches, for example, after the store is closed or in the late evening hours. Further, certain data may be provided at different times based on a data priority. For example, alerts characteristic exceeded a certain threshold and generate a message that is immediately transmitted from server 120 to server 174 whereas the actual monitored data may be transmitted at a later time as a different priority. The data that the server 174 may be stored in a data storage unit 176 and may be retrieved by server 174 or other servers for additional data analysis. The server 174 may communicate via a network 178 with various other devices. For example, server 174 may communicate with a billboard display 182. The billboard display may display the characteristics that are monitored by the sensors located on the product preparation or dispensing devices. In addition, the billboard display may display ambient cleanliness information from the store. The server 174 may communicate with an equipment OEM or repair facility 184. The server 174 may communicate with the equipment OEM or repair request system 184 to request maintenance. Further the system 174 may generate an offer such as an electronic coupon and send the electronic coupon to a user device 180 based on the cleanliness information and additional information including for example the user profile information stored on the server 174 or the remote device 180, the location information related to the electronic device 184 other factors.

Store Clerk

The store clerk may receive notifications for various situations. The determination to transmit the notification may be in the server 120 located in the store 110 and/or by the remote server 174. The store clerk may receive notifications on a mobile or display device through a local network via server 120. The store clerk may receive notifications on various devices through a wide area network via server 120 or remote server 174. Notifications may be triggered in response to various events such as, Bathroom is due for mopping/cleaning, based on defined frequency, Mopping/cleaning time, as scheduled, is missed, Mop is out of place/not stored in defined location, Mop head is due for cleaning, based on defined frequency, Mop head is due for changing, based on defined frequency, Water levels in toilet are above defined threshold, Water levels on floor are above defined threshold (flooding), Toilet paper levels are below defined threshold, Soap levels are below defined threshold, Paper towel supply is below defined threshold, Toilet paper supply is below defined threshold, Consumer throughput is above a defined threshold.

Individual notification triggers can be delivered via any or all of a POS system, Tablet App, Smartphone (App, SMS), Smartwatch (E-Mail), other wearable devices (E-mail, App, notification, SMS). General data may be distributed at the defined frequency, distributed based on a trigger or threshold being exceeded, and accessible any time in dashboard form via any or all of POS system, Tablet App, Smartphone (App, SMS link to Web landing).

Additional data sources that are potentially relevant for the store clerks may include Corporate systems (compliance info, updated process guidelines, other), CPG systems (offer availability), POS data (consumer purchasing history). Potentially amended process/use case for store clerks may include updated compliance information being sent from corporate systems to the store and, in combination with data sent from sensor device(s), the store clerk amends the cleanliness thresholds or dashboard reporting frequencies (or other compliance related metrics) that have been previously set. Another process may include the clerk receiving alert when a purchaser particularly interested in cleanliness (based on profile or preference history) enters the store. If a cleanliness characteristic exceeds a certain threshold, he/she will be prompted to open offer dashboard provided by CPG system, check if an offer is available and, if so, volunteer to the consumer that the offer is available. In another implementation a work order may be issued in response to the purchaser entering the store.

Store Manager

The store manager may receive notifications for various situations. The determination to transmit the notification may be in the server 120 located in the store 110 and/or by the remote server 174. The store manager may receive notifications on a mobile or display device through a local network via server 120. The store manager may receive notifications on various devices through a wide area network via server 120 or remote server 174. Notifications may be triggered based on events such as, Bathroom is due for mopping/cleaning, based on defined frequency, Mopping/cleaning time, as scheduled, is missed, Mop is out of place/not stored in defined location, Mop head is due for cleaning, based on defined frequency, Mop head is due for changing, based on defined saturation levels and/or frequency, Water levels in toilet are above defined threshold, Water levels on floor are above defined threshold (flooding), Toilet paper levels are below defined threshold, Soap levels are below defined threshold, Paper towel supply is below defined threshold, Toilet paper supply is below defined threshold.

Additional collected data from the sensors may be delivered at defined time/time interval(s) and analyzed for sending additional notifications based on a exceeding a threshold (upper, lower, or based on a comparison) of one or more of Number of notification triggers and their type (e.g. toilet paper supply fell below threshold x times in y hours), Time to corrective action, Map of sensors and their plotting across bathroom unit(s), Completed tasks over defined time period (maintenance, cleaning), Average consumer throughput by bathroom unit, Average consumer length of visit (dwell time), Mop duration, across all scheduled cleanings, Mop form, across all scheduled cleanings, Average water level in toilets, Average water level on floor, Average paper towel supply volume, Average toilet paper supply volume, Average soap levels.

Individual notification triggers can be delivered via any or all of POS system, Tablet App, Smartphone (App, SMS), Smartwatch (App, SMS), Other wearable devices (E-mail, App, notification, SMS), Desktop PC (E-Mail, Web Landing Page), Laptop PC (E-Mail, Web Landing Page). General data may be distributed at the defined frequency, distributed based on a trigger or threshold being exceeded, and accessible any time in dashboard form via any or all of POS system, Tablet App, Smartphone (App, SMS link to Web landing), Smartwatch (App, SMS link to Web landing), Other wearable devices (E-mail, App, notification, SMS), Desktop PC (E-Mail, Web Landing Page), Laptop PC (E-Mail, Web Landing Page).

Additional data sources that are potentially relevant for the store managers may include Corporate systems (compliance info, updated process guidelines, other), CPG systems (offer availability), Store systems (clerk performance history), POS system (consumer purchasing history). Potentially amended process/use case for store managers may include updated compliance information being sent from corporate systems to the store and, in combination with data sent from sensor device(s), the store clerk amends the cleanliness parameters (e.g. cleanliness thresholds) that have been set. Another process may include generating information accessible in dashboard form for manager to pull down. Another process may include generating dashboard reports for sensor device, pushed to the manager at a defined frequency, that provide info, graphics, and/or alerts around sensor management and compliance can be a key data point that is used in combination with other clerk performance data to enhance the performance appraisal process.

CPGs

The CPGs or food service vendors may receive notifications for various situations. The determination to transmit the notification may be in the server 120 located in the store 110 and/or by the remote server 174. The CPGs or food service vendors may receive notifications on a mobile or display device through a local network via server 120. The CPGs or food service vendors may receive notifications on various devices through a wide area network via server 120 or remote server 174.

Individual notification triggers can be delivered via any or all of POS system, Tablet App, Smartphone (App, SMS), Smartwatch (App, SMS), Other wearable devices (E-mail, App, notification, SMS), Desktop PC (E-Mail, Web Landing Page), Laptop PC (E-Mail, Web Landing Page). General data may be distributed at the defined frequency, distributed based on a trigger or threshold being exceeded, and accessible any time in dashboard form via any or all of POS system, Tablet App, Smartphone (App, SMS link to Web landing), Smartwatch (App, SMS link to Web landing), Other wearable devices (E-mail, App, notification, SMS), Desktop PC (E-Mail, Web Landing Page), Laptop PC (E-Mail, Web Landing Page).

Additional data sources that are potentially relevant for the CPGs may include a POS system (consumer purchasing history). Potentially amended process/use cases for CPGs may include analyzing the propensity for loyal consumers to purchase or enter store, as a function of cleanliness, are made available to the CPG (hence answering the question—how effective are cleanliness driven product offers or messages).

Consumers

The consumers may receive notifications for various situations. The determination to transmit the notification may be in the server 120 located in the store 110 and/or by the remote server 174. The consumers may receive notifications on a mobile or display device through a local network via server 120. The consumers may receive notifications on various devices through a wide area network via server 120 or remote server 174. Notifications may be triggered based on events such as, Bathroom is vacant, and Bathroom is busy.

Additional collected data from the sensors may be delivered at defined time/time interval(s) and analyzed for sending additional notifications based on a exceeding a threshold (upper, lower, or based on a comparison) of one or more of a, Last time bathroom was mopped/cleaned, Average bathroom usage/throughput, General bathroom statistics (mop/clean rate, soap levels, paper towel/toilet paper inventory)

Individual notification triggers can be delivered via any or all of an Electronic LED, Tablet App, Smartphone (App, SMS), Smartwatch (App, SMS), Other wearable devices (E-mail, App, notification, SMS), Smart car infotainment (App, Alert). General data may be distributed at the defined frequency and accessible any time via any or all of an Electronic LED, Tablet App, Smartphone (App, SMS link to Web landing), Smartwatch (App, SMS link to Web landing), Desktop PC (E-Mail, Web Landing Page), Laptop PC (E-Mail, Web Landing Page)

Equipment OEMs

The equipment OEMs or repair services may receive notifications for various situations. The determination to transmit the notification may be in the server 120 located in the store 110 and/or by the remote server 174. The equipment OEMs or repair services may receive notifications on a mobile or display device through a local network via server 120. The equipment OEMs or repair services may receive notifications on various devices through a wide area network via server 120 or remote server 174. Notifications may be triggered based on events such as, Maintenance failure/work order request required, Toilet paper inventory is below defined threshold, Soap inventory is below defined threshold, Paper towel inventory is below defined threshold, Replacement mop head inventory is below defined threshold, Replacement mop inventory is below defined threshold.

Additional collected data from the sensors may be delivered at defined time/time interval(s) and analyzed for sending additional notifications based on a exceeding a threshold (upper, lower, or based on a comparison) of one or more of Average paper towel supply volume, Average toilet paper supply volume, Average soap levels.

Individual notification triggers can be delivered via any or all of, Tablet App, Smartphone (App, SMS), Smartwatch (App, SMS), Desktop PC (E-Mail, Web Landing Page), Laptop PC (E-Mail, Web Landing Page). General data may be distributed at the defined frequency, distributed based on a trigger or threshold being exceeded, and accessible any time in dashboard form via any or all of Tablet App, Smartphone (App, SMS link to Web landing), Smartwatch (App, SMS link to Web landing), Desktop PC (E-Mail, Web Landing Page), Laptop PC (E-Mail, Web Landing Page).

The server 120 and/or server 174 includes communication interfaces 202, system circuitry 204, input/output (I/O) interfaces 206, and display circuitry 208 that generates user interfaces 210 locally or for remote display, e.g., in a web browser running on a local or remote machine through which a project is defined and resources are selected, evaluated, allocated, and connected to a project. The user interfaces 210 and the I/O interfaces 206 may include graphical user interfaces (GUIs), touch sensitive displays, voice or facial recognition inputs, buttons, switches, speakers and other user interface elements. Additional examples of the I/O interfaces 206 include microphones, video and still image cameras, headset and microphone input/output jacks, Universal Serial Bus (USB) connectors, memory card slots, and other types of inputs. The I/O interfaces 206 may further include magnetic or optical media interfaces (e.g., a CDROM or DVD drive), serial and parallel bus interfaces, and keyboard and mouse interfaces.

The communication interfaces 202 may include wireless transmitters and receivers ("transceivers") 212 and any antennas 214 used by the transmit and receive circuitry of the transceivers 212. The transceivers 212 and antennas 214 may support WiFi network communications, for instance, under any version of IEEE 802.11, e.g., 802.11n or 802.11ac. The communication interfaces 202 may also include wireline transceivers 216. The wireline transceivers 216 may provide physical layer interfaces for any of a wide range of communication protocols, such as any type of Ethernet, data over cable service interface specification (DOCSIS), digital subscriber line (DSL), Synchronous Optical Network (SONET), or other protocol.

The system circuitry 204 may include any combination of hardware, software, firmware, or other circuitry. The system circuitry 204 may be implemented, for example, with one or more systems on a chip (SoC), application specific integrated circuits (ASIC), microprocessors, discrete analog and digital circuits, and other circuitry. The system circuitry 204 is part of the implementation of any desired functionality in the server 120 and/or server 174. As just one example, the system circuitry 204 may include one or more instruction processors 218 and memories 220. The memory 220 stores, for example, control instructions 222 and an operating system 224. In one implementation, the processor 218 executes the control instructions 222 and the operating system 224 to carry out any desired functionality for the server 120 and/or server 174. The control parameters 226 provide and specify configuration and operating options for the control instructions 222, operating system 224, and other functionality of the server 120 and/or server 174.

The server 120 and/or server 174 may include a local data repository 232 that includes volume storage devices, e.g., hard disk drives (HDDs) and solid state disk drives (SDDs). The storage devices may define and store databases that the control instructions 222 access, e.g., through a database control system, to perform the functionality implemented in the control instructions 222. In the example shown, the databases include a resource data database 228 and a project data database 230. In other implementations, any of the databases may be part of a single database structure, and, more generally, may be implemented logically or physically in many different ways. Each of the databases defines tables storing records that the control instructions 222 read, write, delete, and modify to perform the processing noted below. The resources descriptors may maintain their own resource descriptor data repositories. The system circuitry 204 may implement the resource analysis circuitry 114, project platform circuitry 116, and the operator control circuitry 118, e.g., as control instructions 222 executed by the processor 218.

The thresholds and alerts may be stored in one or more data bases and may be associated with the sensor or device. For example, separate thresholds for each cleanliness characteristic may be stored for each sensor in a sensor record. Separate thresholds for characteristic of a device may be stored for each device in a device record.

Similar offers such as electronic coupons, in store advertisements or POS offers may be stored in records related to the sensor, or device (e.g. mop), or a purchaser profile. Further, the offers may be generated and/or delivered in response to characteristics from or combinations of characteristics from the sensor characteristic, device characteristic, and a purchaser profile. Redemptions of electronic coupons and or purchases corresponding with in store advertisements may be tracked and analyzed with respect to the characteristics (e.g. last bathroom cleaning, full toilet paper dispensers, paper towel dispensers) that were used to generate and/or deliver the offer. As such, the usefulness of the offers may be maximized. This may even be controlled in a feedback loop where the thresholds are adjusted based on redemption data and/or purchase correlation data.

The methods, devices, processors, modules, engines, and logic described above may be implemented in many different ways and in many different combinations of hardware and software. For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

As a person skilled in the art will readily appreciate, the above description is meant as an illustration of implementation of the principles this disclosure. This description is not intended to limit the scope or application of this system in that the system is susceptible to modification, variation and change, without departing from the spirit of this disclosure, as defined in the following claims.

We claim:

1. A system for monitoring cleanliness of a retail store, the system comprising:
   a server;
   a database in communication with the server and storing cleanliness parameters;
   at least one sensor configured to transmit measured cleanliness characteristics to the server, wherein the server is configured to generate and transmit a message based on a location of the consumer and a comparison of the measured cleanliness characteristics and the cleanliness parameters stored in the database.

2. The system according to claim 1, wherein the message is transmitted to a consumer in response to a profile associated with the consumer including a cleanliness importance setting.

3. The system according to claim 1, wherein the message is transmitted by the server to a store clerk, a store manager, or an equipment service company.

4. The system according to claim 1 wherein the at least one sensor is configured to measure a location of a mop.

5. The system according to claim 4, wherein the at least one sensor is configured to measure a pressure applied to the mop.

6. The system according to claim 4, wherein the at least one sensor comprises three sensors located at different positions and the server is configured to triangulate a location of the mop based on the three sensors.

7. The system according to claim 1, wherein the at least one sensor is configured to measure a water overflow.

8. The system according to claim 1, wherein the at least one sensor is configured to measure a door usage.

9. The system according to claim 1, wherein the at least one sensor is configured to measure a sink usage.

10. The system according to claim 1, wherein the at least one sensor is configured to measure a toilet usage.

11. The system according to claim 1, wherein the at least one sensor is configured to measure an amount of paper towels or toilet paper remaining in a dispenser.

12. A system for monitoring cleanliness of a retail store, the system comprising:
    a server;
    a database in communication with the server and storing mop usage parameters;
    at least one sensor configured to transmit mop usage characteristics to the server, wherein the server is configured to generate and transmit a message to a consumer based on a location of the consumer and a comparison of the measured mop usage characteristics and the mop usage parameters stored in the database.

13. The system according to claim 12, wherein the at least one sensor comprises three sensors located at different positions and the server is configured to triangulate a location of the mop based on the three sensors.

14. A system for monitoring cleanliness of a retail store, the system comprising:
- a server;
- at least one database in communication with the server, the at least one database storing a consumer profile for a consumer including a cleanliness importance parameter and a cleanliness parameters;
- at least one sensor configured to transmit measured cleanliness characteristics to the server, wherein the server is configured to generate and transmit a message to the consumer based on the cleanliness importance parameter, a location of the consumer, and a comparison of the measured cleanliness characteristics and the cleanliness parameters stored in the database.

* * * * *